(12) United States Patent
Ohnishi et al.

(10) Patent No.: US 6,269,263 B1
(45) Date of Patent: Jul. 31, 2001

(54) METHOD FOR ESTIMATING HEART RATE VARIABILITY AND APPARATUS FOR EMBODYING ESTIMATION

(75) Inventors: Noboru Ohnishi; Allan Kardec Barros, both of Nagoya (JP)

(73) Assignee: Riken, Saitama (JP)

(*) Notice: Subject to any disclaimer, the term of this patent is extended or adjusted under 35 U.S.C. 154(b) by 0 days.

(21) Appl. No.: 09/457,359

(22) Filed: Dec. 9, 1999

(30) Foreign Application Priority Data

Dec. 11, 1998 (JP) ................................................. 10-352428

(51) Int. Cl.[7] ........................................................ A61B 5/04
(52) U.S. Cl. ................................................................ 600/518
(58) Field of Search ..................................... 600/509, 515, 600/518, 519

(56) References Cited

U.S. PATENT DOCUMENTS 5,291,400 * 3/1994 Gilham .
5,423,325 * 6/1995 Burton .

OTHER PUBLICATIONS

"Straight–Tempo: A Universal Tool to Manipulate Linguistic and Para–Linguistic Speech Information", ATR HIP Res. Labs., 1997 vol. 2 of 2 by Hideki Kawahara.

* cited by examiner

*Primary Examiner*—Scott Getzow
(74) *Attorney, Agent, or Firm*—Birch, Stewart, Kolasch & Birch, LLP

(57) ABSTRACT

In order to provide a method for estimating a heart rate variability and the apparatus for embodying such estimation which can be operated at a low sampling frequency without detecting peaks on a waveform in electrocardiogram data, a method for estimating a heart rate variability from electrocardiogram data is arranged in such that frequencies in each of which a spectrum is maximum at a predetermined time are detected from the electrocardiogram data, and a heart rate variability is estimated on the basis of results obtained by filtering the electrocardiogram data with a band pass filter including the frequency detected as its center frequency.

6 Claims, 4 Drawing Sheets

METHOD FOR ESTIMATING HEART RATE VARIABILITY AND APPARATUS FOR EMBODYING ESTIMATION

BACKGROUND OF THE INVENTION

1. Field of The Invention

The present invention relates to a method for estimating a heart rate variability and an apparatus for embodying such estimation, and more particularly to a method for estimating a heart rate variability and an apparatus for embodying such estimation which can be operated at a low sampling frequency and by which a heart rate variability (HRV) can be easily estimated from electrocardiogram data.

2. Description of The Related Art

In the field of medical procedure, HRV has been utilized heretofore in a diagnosis for heart diseases and the like. In this respect, a variety of manners for estimating an HRV from electrocardiogram data have been proposed.

As a conventional manner for estimating an HRV from electrocardiogram data, for example, a manner for estimating an HRV wherein peaks R on a waveform are detected from electrocardiogram data as shown in FIG. 1, and an inverse number of a time interval between peaks R is multiplied by 60 for estimating the number of beat in heart beats per minute has been known.

More specifically, in the above described manner, when it is assumed that a time instant when a peak R appears is represented by $t_i$ (i=0, 1, ..., n), an HRV is determined by vectors $[60/(t_1-t_0), 60/(t_2-t_1), ..., 60/(t_n-t_{n-1})]^t$.

Accordingly, peaks R on a waveform must be detected correctly from electrocardiogram data in the above described conventional manner, so that such a problem that a sampling frequency for detecting peaks R on a waveform becomes high in the case where an apparatus for estimating an HRV is constituted by utilizing a conventional manner, resulting in a complicated structure of the apparatus, besides it results in a high cost has been pointed out.

OBJECTS AND SUMMARY OF THE INVENTION

The present invention has been made in view of a problem involved in the prior art as described above, and an object of the invention is to provide a method for estimating a heart rate variability and the apparatus for embodying such estimation which can be operated at a low sampling frequency without detecting peaks on a waveform in electrocardiogram data.

In order to achieve the above described object, a method for estimating a heart rate variability from electrocardiogram data according to the present invention is constituted in such that frequencies in each of which a spectrum is maximum at a predetermined time are detected from the electrocardiogram data, and a heart rate variability is estimated on the basis of results obtained by filtering the electrocardiogram data with a band pass filter including the frequency detected as its center frequency.

Accordingly, there is no need of detecting peaks on a waveform in electrocardiogram data in accordance with a method for estimating a heart rate variability of the present invention.

Furthermore, a method for estimating a heart rate variability from electrocardiogram data according to the present invention is constituted in such that frequencies in each of which a spectrum is maximum at a predetermined time are detected from the electrocardiogram data, and a heart rate variability is estimated from a value acquired by multiplying an instantaneous angular frequency determined with use of Hilbert transform by a constant (60/2 π) on the basis of results obtained by filtering the electrocardiogram data with a band pass filter including the frequency detected as its center frequency.

Accordingly, there is no need of detecting peaks on a waveform in electrocardiogram data in accordance with a method for estimating a heart rate variability of the present invention.

With respect to the above description, when frequencies in each of which a spectrum is maximum at a predetermined time are detected from the electrocardiogram data, the detection may be conducted within a predetermined variable range.

Moreover, an apparatus for estimating a heart rate variability from electrocardiogram data according to the present invention comprises a detection means for detecting from electrocardiogram data frequencies in each of which a spectrum is maximum at a predetermined time, and a band pass filter including the frequency detected by the detection means as its center frequency, wherein a heart rate variability is estimated on the basis of results obtained by filtering the electrocardiogram data with the band pass filter.

Accordingly, there is no need of detecting peaks on a waveform in electrocardiogram data in accordance with an apparatus for estimating a heart rate variability of the present invention.

Furthermore, an apparatus for estimating a heart rate variability from electrocardiogram data according to the present invention comprises a detection means for detecting from electrocardiogram data frequencies in each of which a spectrum is maximum at a predetermined time, a band pass filter including a frequency detected by the detection means as its center frequency, and an instantaneous angular frequency acquiring means for determining an instantaneous angular frequency with the use of Hilbert transform from results obtained by filtering the electrocardiogram data by means of the band pass filter, and a multiplying means for multiplying the instantaneous angular frequency determined by the instantaneous angular frequency acquiring means by a constant (60/2 π), wherein a value produced from multiplication of the instantaneous angular frequency, determined by the instantaneous angular frequency acquiring means with the use of Hilbert transform from the results obtained by, filtering the electrocardiogram data by means of the band pass filter, by the constant (60/2 π) is estimated as a heart rate variability.

Accordingly, there is no need of detecting peaks on a waveform in electrocardiogram data in accordance with an apparatus for estimating a heart rate variability of the present invention.

With respect to the above description, when frequencies in each of which a spectrum is maximum at a predetermined time are detected from the electrocardiogram data, the detection means may detect a predetermined variable range.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

An example of preferred embodiments of a method for estimating a heart rate variability and the apparatus for embodying such estimation according to the present invention will be described in detail hereinafter in conjunction with the accompanying drawings.

Figure 2:
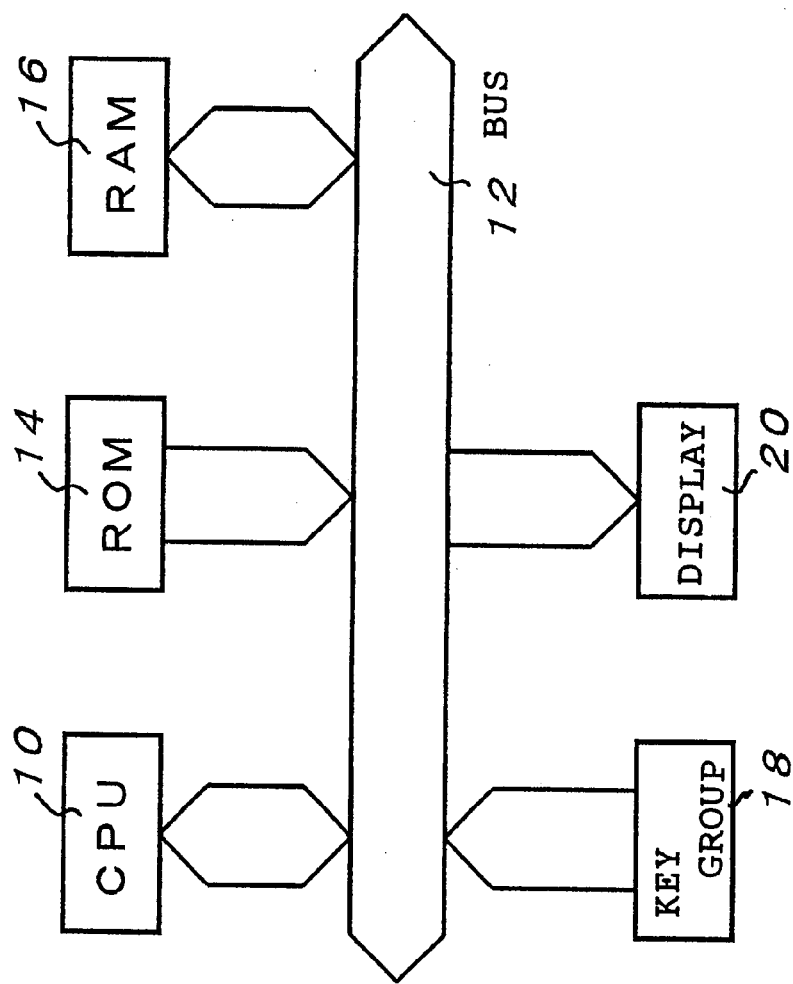
FIG. 2 is a block constitutional explanatory diagram showing an example of preferred embodiments of an apparatus for estimating a heart rate variability according to the present invention.

FIG. 2 is a block constitutional explanatory diagram showing an example of preferred embodiments of an apparatus for estimating a heart rate variability according to the present invention.

Specifically, the apparatus for estimating a heart rate variability is constituted in such that control for the whole operations are made by means of a central processing unit (CPU) 10, and to the CPU 10 are connected through a bus 12 a read only memory (ROM) 14 for storing a program and the like executed by the CPU 10, a random access memory (RAM) 16 functioning as a working area for the CPU 10, a key group 18 composed of a variety of keys which will be mentioned later, and a display 20 for displaying an electrocardiogram and the like, respectively.

Figure 3:
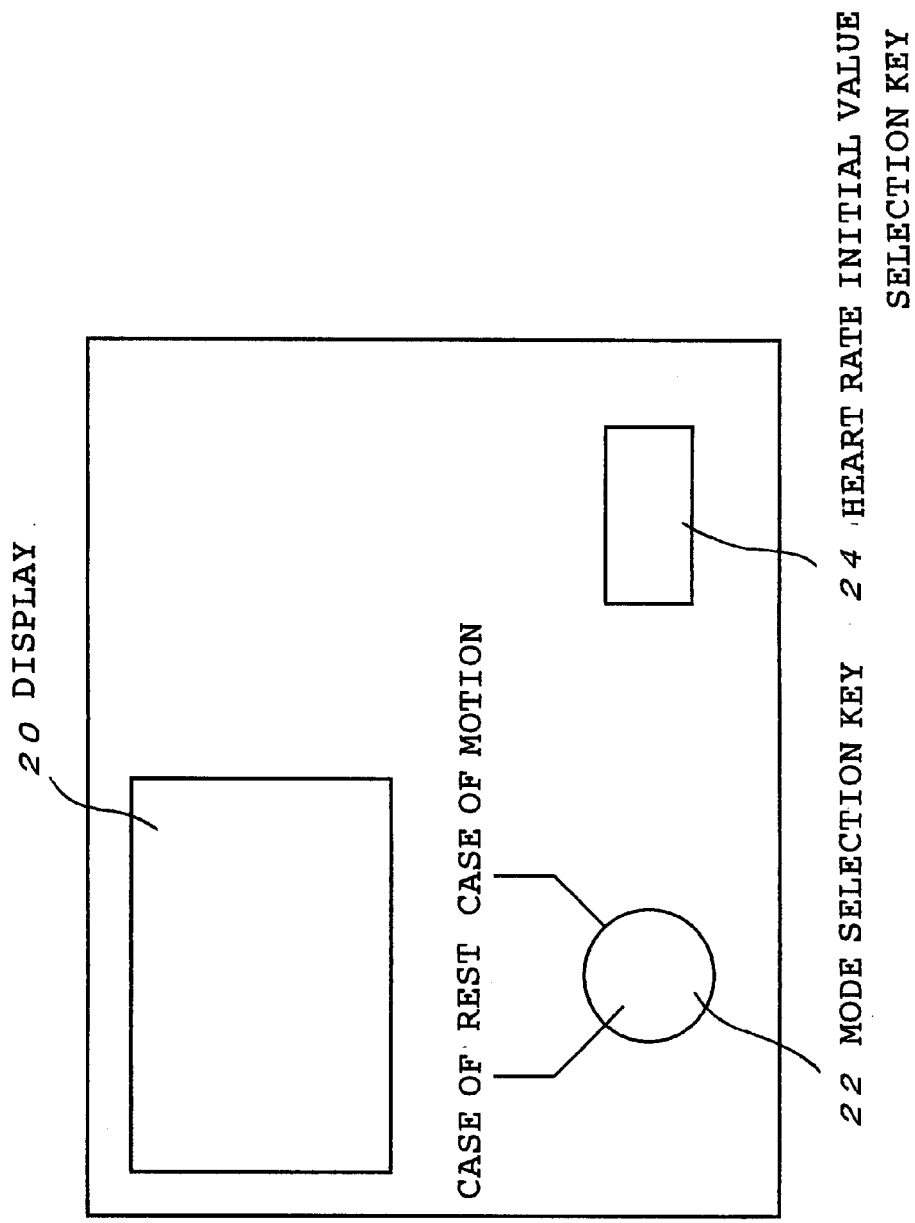
FIG. 3 is a schematic constitutional explanatory view showing a console panel of an apparatus for estimating a heart rate variability according to the present invention.

It is to be noted herein that only the keys relating to practice of the present invention are illustrated in FIG. 3, while the keys which do not relate to practice of the present invention are not illustrated and the explanation therefor is omitted with respect to a variety of keys composing the key group 18.

More specifically, provided are a mode selection key 22 for selecting a mode wherein measurement for electrocardiogram data is conducted in either a case of "resting" or a case of "motion", and a heart rate initial value selection key 24 for selecting an initial value ($f_0$) of heart rate.

In these circumstances, when measurement of electrocardiogram data is conducted at 5 Hz sampling frequency, "resting" mode is selected by means of the mode selection key 22, while when measurement of electrocardiogram data is conducted at 20 Hz sampling frequency, "motion" mode is to be selected by means of the mode selection key 22.

Figure 4:
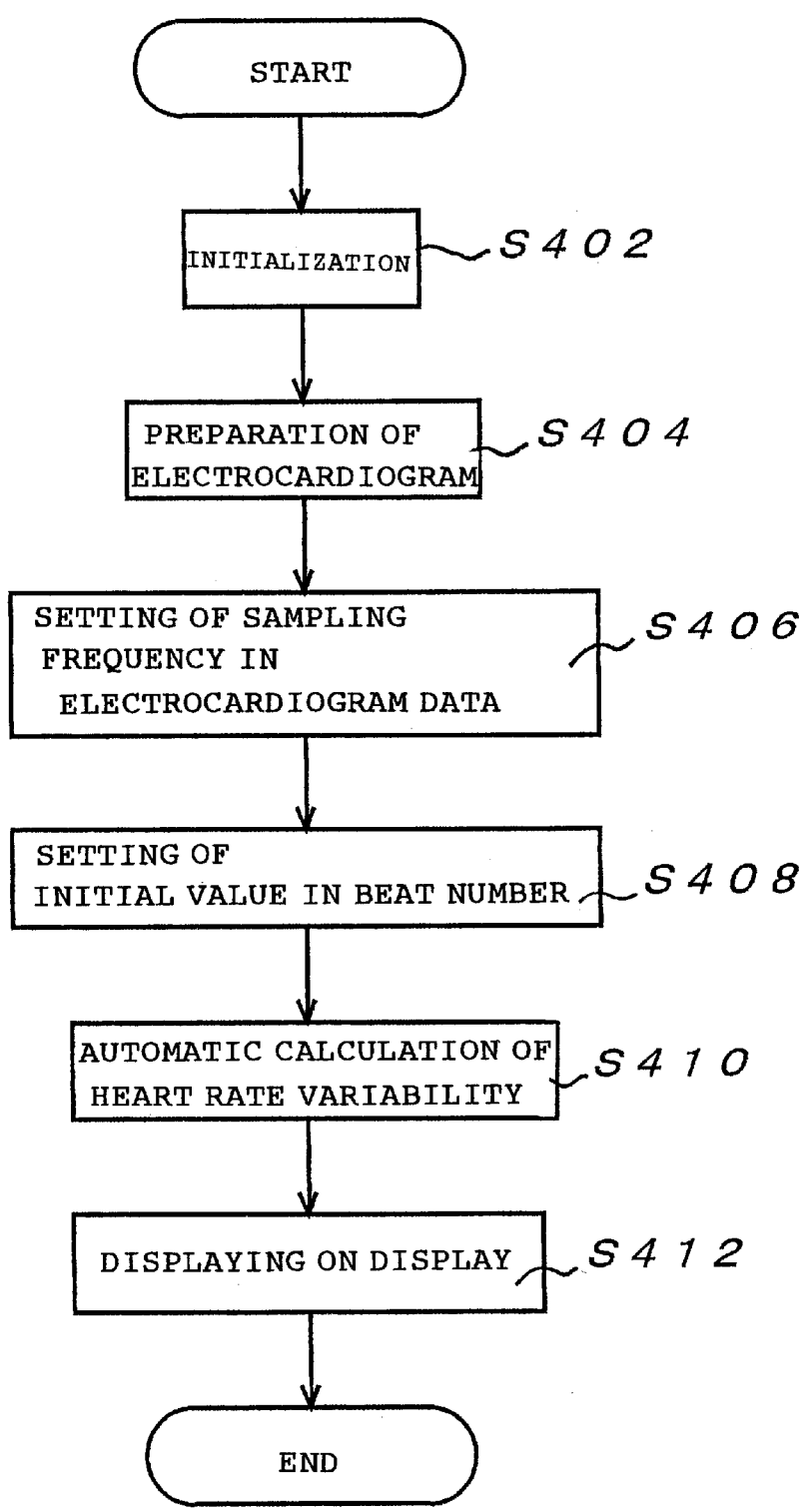
FIG. 4 is a flowchart showing operations of an apparatus for estimating a heart rate variability according to the present invention.

In accordance with the constitution described above, operations of the apparatus for estimating a heart rate variability will be explained by referring to a flowchart shown in FIG. 4.

Figure 1:
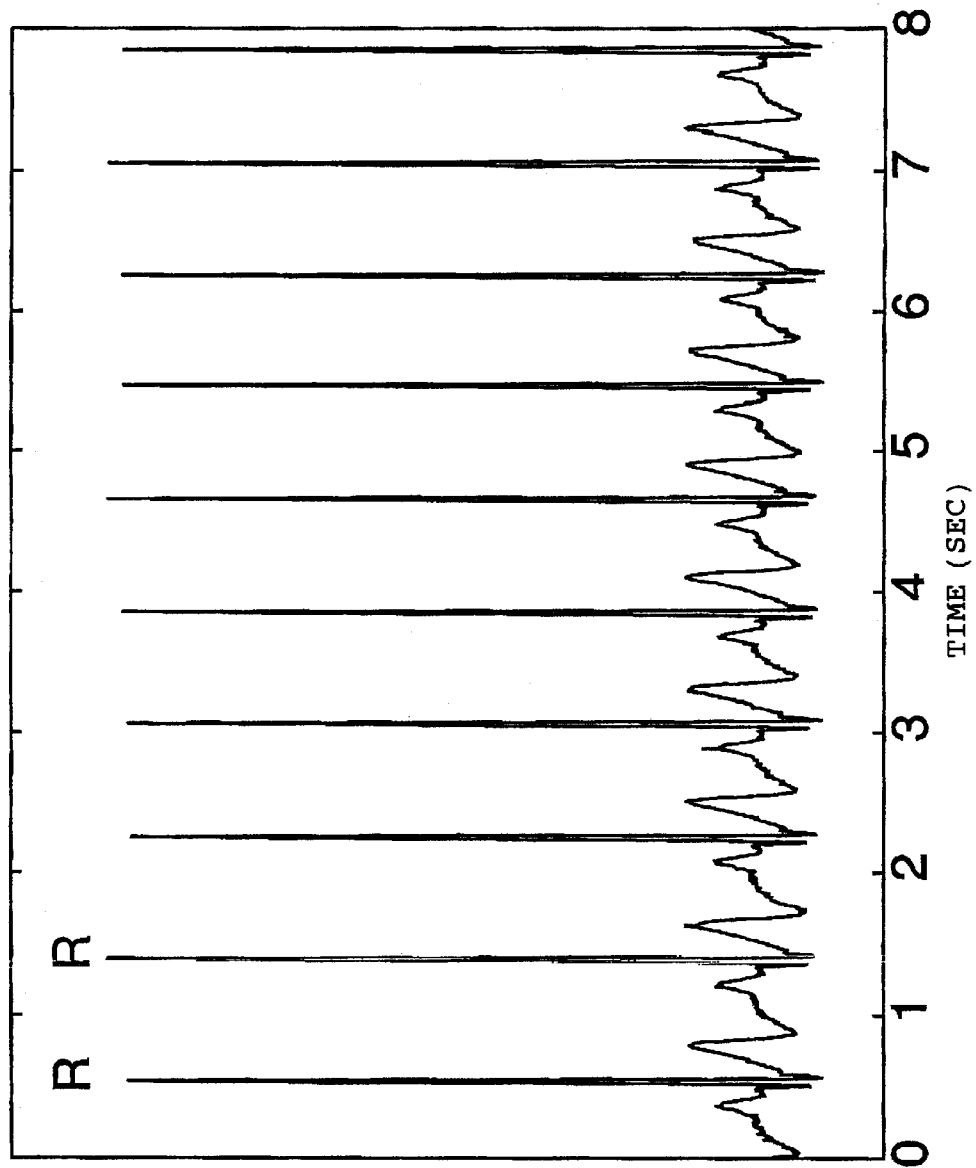
FIG. 1 is a waveform diagram showing an example of electrocardiogram data.

Namely, in the apparatus for estimating a heart rate variability, when initialization for clearing resisters and flags which have been prepared in a working area is effected (step S402), electrocardiogram data are measured to make out an electrocardiogram as shown in FIG. 1 (step S404).

In measuring electrocardiogram data, it is arranged herein in such that measurement of the electrocardiogram data is conducted at 5 Hz sampling frequency in case of rest, while measurement thereof is conducted at 20 Hz sampling frequency in case of motion.

In this respect, since a well-known technique can be utilized for processing with reference to measurement and preparation of electrocardiogram data, the detailed description therefor is omitted.

Then, it is set out that measurement of electrocardiogram data was conducted either in case of a resting mode, i.e., it was conducted at 5 Hz sampling frequency, or in case of a motion mode, i.e., it was conducted at 20 Hz sampling frequency (step S406).

In this case, setting of a key in the step S406 is implemented by operating the mode selection key 22 with a user in an apparatus for estimating a heart rate variability. More specifically, when the mode selection key 22 is set "in case of resting" by the user, such setting that the measurement of electrocardiogram data was carried out at 5 Hz sampling frequency is established, while when the mode selection key 22 is set "in case of motion" by the user, such setting that the measurement of electrocardiogram data was carried out at 20 Hz sampling frequency is established.

A next step is the one for processing of setting an initial value $f_0$ of heart rate (step S408).

Details of processing for setting an initial value $f_0$ of heart rate will be described herein. A sampling frequency is divided by 2 in the event where electrocardiogram data are measured in case of motion. If it is not divided, a spectrogram of the electrocardiogram data is calculated within a range of frequencies from 1 Hz to 3 Hz without any modification, and three peaks are to be found on spectral at the initial time instant (time instant $t=t_0$). The peak frequencies thus obtained are displayed on the display 20, and any frequency is selected from these three peak frequencies by a user with the use of the heart rate initial value selection key 24 as the initial value $f_0$ of heart rate, and this initial value is input, whereby the initial value $f_0$ of heart rate is set out.

In the next step, a heart rate variability is calculated automatically with respect to all the electrocardiogram data (step S410).

In processing for calculating automatically the heart rate variability, first, a frequency $f_1$ is determined in which a spectrum becomes maximum within a variable range of from a frequency ($f_0$−0.5) Hz to a frequency ($f_0$+0.5) Hz at the time instant next to the initial time instant, i.e., a second time instant (time instant $t=t_1$). Thereafter, such processing as described above is repeated at respective time instants, so that a frequency in which a spectrum is maximum at each time instant is determined.

More specifically, when it is assumed that a present time instant to be processed is the i-th time instant (time instant $t=t_i$) in the respective time instants, and in this situation, if a frequency having a spectrum which was detected as the maximum at the preceding time instant with respect to the i-th time instant (time instant $t=t_i$), i.e., the (i−1)-th time instant (time instant $t=t_{i-1}$) is assigned to be a frequency $f_{i-1}$ Hz, a frequency $f_i$ at which a spectrum is maximum is detected within a range of from ($f_{i-1}$−0.5) Hz to ($f_{i-1}$+0.5), and the frequency $f_i$ thus detected is considered to be the frequency having the maximum spectrum at the i-th time instant (time instant $t=t_i$) being the time instant to be processed.

In this respect, a frequency (including initial value $f_0$) having the maximum spectrum at each of the time instants obtained as described above is referred to as fundamental frequency.

When the above described processing is repeated, time sequence of the fundamental frequency ($f_0, f_1, \ldots, f_n$) can be obtained, and the time sequence of the fundamental frequency is referred to as "driver".

After thus obtaining the driver, electrocardiogram data are allowed to pass through a band pass filter containing a frequency of the driver as its center frequency to filter the data, and a value obtained by multiplying an instantaneous angular frequency, determined from the result of the filtering with the use of, for example, Hilbert transform, by a constant ($60/2\ \pi$) is estimated as a heart rate variability (HRV).

Then, the HRV estimated in the above described step S410 is displayed on the display 20 (step S412).

Accordingly, an HRV can be estimated without detecting peaks R on a waveform of electrocardiogram data in the above described preferred embodiments unlike a conventional method for estimating an HRV.

In other words, a fundamental frequency of electrocardiogram data being a time series signal is estimated as a driver, and a beat number is obtained therefrom.

As a result, when the method of the present invention is compared with a conventional method for estimating an HRV, the former method can lower a sampling frequency, resulting in simplification of a constitution of equipment, whereby it becomes possible to reduce a cost therefor.

The lowest sampling frequency is 128 Hz in a conventional method for estimating an HRV, while 5 Hz is sufficient for a method of the present preferred embodiment, so that a value of sampling frequency can be reduced to about twentieth part of that in the conventional method.

Since the present invention has been constituted as described above, it results in such an excellent advantage of providing a method for estimating a heart rate variability and an apparatus therefor which can be operated at a low sampling frequency without detecting peaks on a waveform in an electrocardiogram.

It will be appreciated by those of ordinary skill in the art that the present invention can be embodied in other specific forms without departing from the spirit or essential characteristics thereof.

The presently disclosed embodiments are therefore considered in all respects to be illustrated and not restrictive. The scope of the invention is indicated by the appended claims rather than the foregoing description, and all changes that come within the meaning and range of equivalents thereof are intended to be embraced therein.

The entire disclosure of Japanese Patent Application No. 10-352428 filed on Dec. 11, 1998 including specification, claims, drawings and summary are incorporated herein by reference in its entirety.

What is claimed is:

1. A method for estimating a heart rate variability from electrocardiogram data, comprising:

frequencies in each of which a spectrum is maximum at a predetermined time being detected from the electrocardiogram data, and a heart rate variability being estimated on the basis of results obtained by filtering said electrocardiogram data with a band pass filter including said frequency detected as its center frequency.

2. A method for estimating a heart rate variability from electrocardiogram data, comprising:

frequencies in each of which a spectrum is maximum at a predetermined time being detected from the electrocardiogram data, and a heart rate variability being estimated from a value acquired by multiplying an instantaneous angular frequency determined with use of Hilbert transform by a constant ($60/2\ \pi$) on the basis of results obtained by filtering said electrocardiogram data with a band pass filter including said frequency detected as its center frequency.

3. A method for estimating a heart rate variability as claimed in any one of claims 1 and 2, wherein:

when frequencies in each of which a spectrum is maximum at a predetermined time are detected from said electrocardiogram data, the detection may be conducted within a predetermined variable range.

4. An apparatus for estimating a heart rate variability from electrocardiogram data, comprising:

a detection means for detecting from electrocardiogram data frequencies in each of which a spectrum is maximum at a predetermined time, and a band pass filter including the frequency detected by said detection means as its center frequency, wherein:

a heart rate variability is estimated on the basis of results obtained by filtering said electrocardiogram data with said band pass filter.

5. An apparatus for estimating a heart rate variability from electrocardiogram data, comprising:

a detection means for detecting from electrocardiogram data frequencies in each of which a spectrum is maximum at a predetermined time, a band pass filter including the frequency detected by said detection means as its center frequency, and an instantaneous angular frequency acquiring means for determining an instantaneous angular frequency with the use of Hilbert transform from results obtained by filtering said electrocardiogram data by means of said band pass filter, and a multiplying means for multiplying the instantaneous angular frequency determined by said instantaneous angular frequency acquiring means by a constant ($60/2\ \pi$), wherein:

a value produced from multiplication of the instantaneous angular frequency, determined by said instantaneous angular frequency acquiring means with the use of Hilbert transform from the results obtained by filtering said electrocardiogram data by means of said band pass filter, by the constant ($60/2\ \pi$) is estimated as a heart rate variability.

6. An apparatus for estimating a heart rate variability as claimed in any one of claims 4 and 5, wherein:

when frequencies in each of which a spectrum is maximum at a predetermined time are detected from said electrocardiogram data, said detection means may detect a predetermined variable range.

* * * * *